United States Patent [19]

Sayers

[11] 3,983,234

[45] Sept. 28, 1976

[54] TREATMENT OF DYSKINESIAS

[75] Inventor: Anthony Campbell Sayers, Koniz, Switzerland

[73] Assignee: Sandoz Ltd., Basel, Switzerland

[22] Filed: June 25, 1975

[21] Appl. No.: 590,146

[30] Foreign Application Priority Data

July 4, 1974 Switzerland.......................... 9202/74

[52] U.S. Cl................................. 424/250; 424/319
[51] Int. Cl.² .............. A61K 31/495; A61K 31/495
[58] Field of Search............................ 424/319, 250

[56] References Cited
UNITED STATES PATENTS
3,701,829  10/1972  Bartholini ........................... 424/319

OTHER PUBLICATIONS
Chem. Abst., vol. 76, 42035q, (1972).

*Primary Examiner*—Stanley J. Friedman
*Attorney, Agent, or Firm*—Gerald D. Sharkin; Robert S. Honor; Thomas O. McGovern

[57]        ABSTRACT

Clozapine is useful in the treatment of dyskinesias.

5 Claims, 4 Drawing Figures

CLOZ = CLOZAPINE
HAL = HALOPERIDOL
APO = APOMORPHINE

TREATMENT OF DYSKINESIAS

The present invention relates to a new therapeutic use of the compound 8-chloro-11-(4-methyl-1-piperazinyl)-5H-dibenzo[b,e][1,4]diazepine (clozapine) in the suppression of dyskinesias induced by dopaminergic substances, such as DOPA [3-(3,4-dihydroxyphenyl)-L-alanine] used for the treatment of Parkinson's disease, as indicated by a suppression of the hypersensitiveness of DA receptors, but without any blocking of these receptors, in the following tests in rats on administration of from 0.4 to 80 mg/kg animal body weight daily.

The favourable effect of clozapine is indicated inter ali in tests conducted with rats in which a unilateral lesion of the corpus striatum has been performed.

FIGURE EXPLANATIONS

Figure 1:
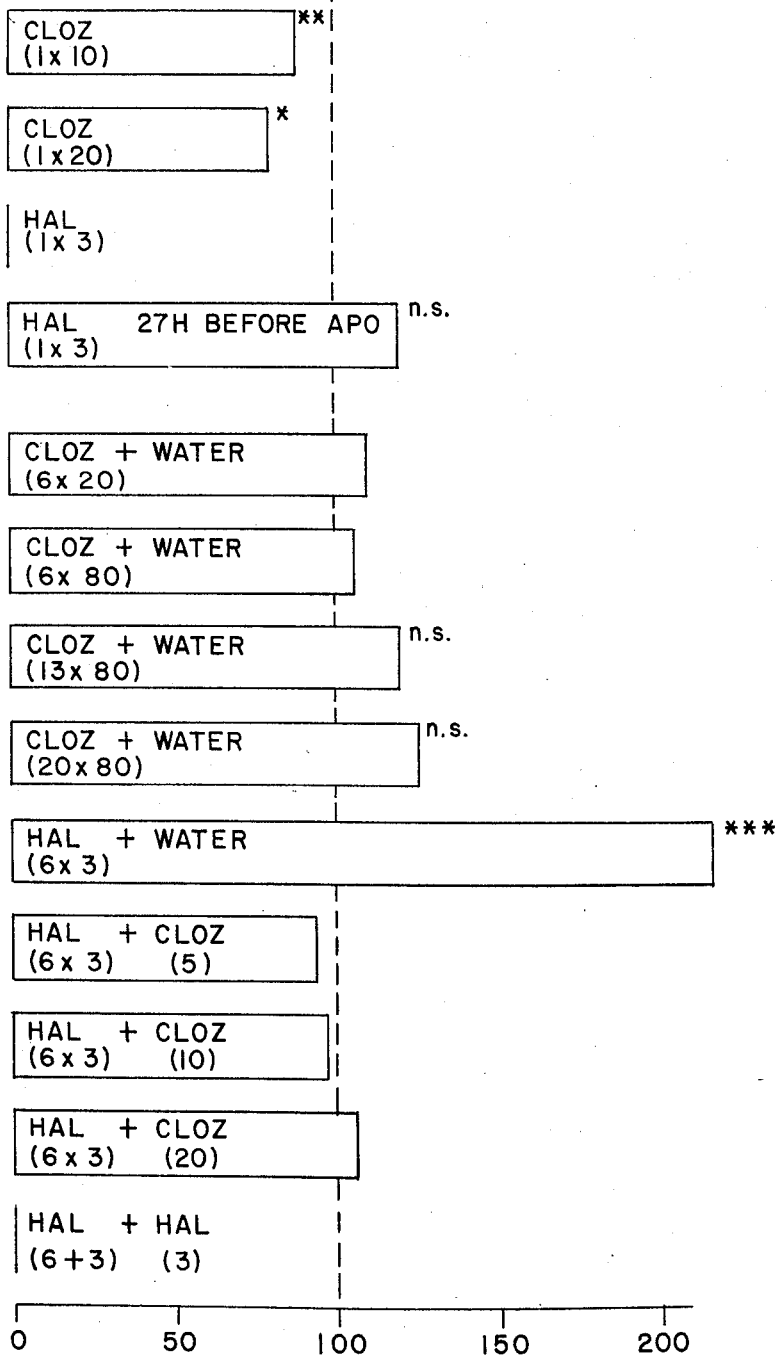

FIG. 1: Turning movements after apomorphine in rats with unilateral lesions in the striatum. Influence by single and repeated administration of haloperidol and/or clozapine (doses in mg/kg p.o.).

Apomorphine (0.4 mg/kg s.c.) was administered 3 hours after the last treatment. n.s. = insignificant; *p <0.05; p<0.01; *p<0.001.

Figure 2:
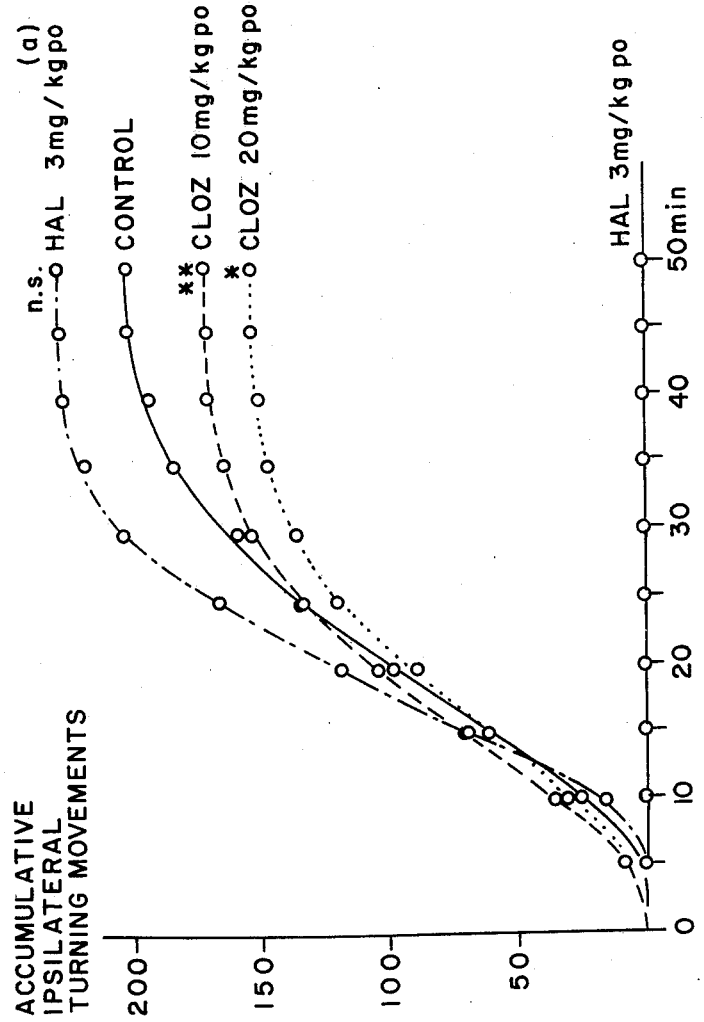

FIG. 2: Turning movements after apomorphine in rats with unilateral lesions in the striatum. Pretreatment by a single administration of clozapine or haloperidol.

Apomorphine (0.4 mg/kg s.c.) was administered 3 hours (a) 27 hours) after clozapine or haloperidol. n.s. = insignificant; * p 0.05; **p 0.01 (Wilcoxon test for pair differences).

Figure 3:
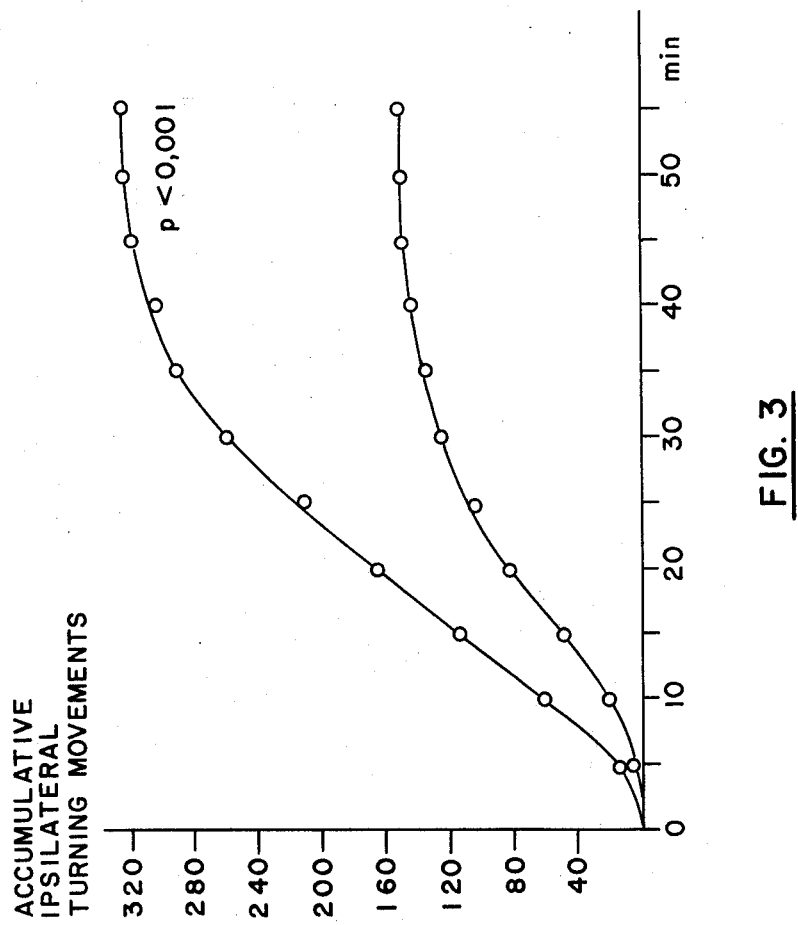

FIG. 3: Turning movements after apomorphine in rats with unilateral lesions in the striatum. Pretreatment by repeated administration of haloperidol.
0—0 haloperidol 6 × 3 mg/kg p.o. + water on seventh day.
0—0 water 6 × 10 cc/kg p.o. + water on seventh day.
Apomorphine was administered (0.4 mg/kg s.c.) 3 hours after treatment on the seventh day.

Figure 4:
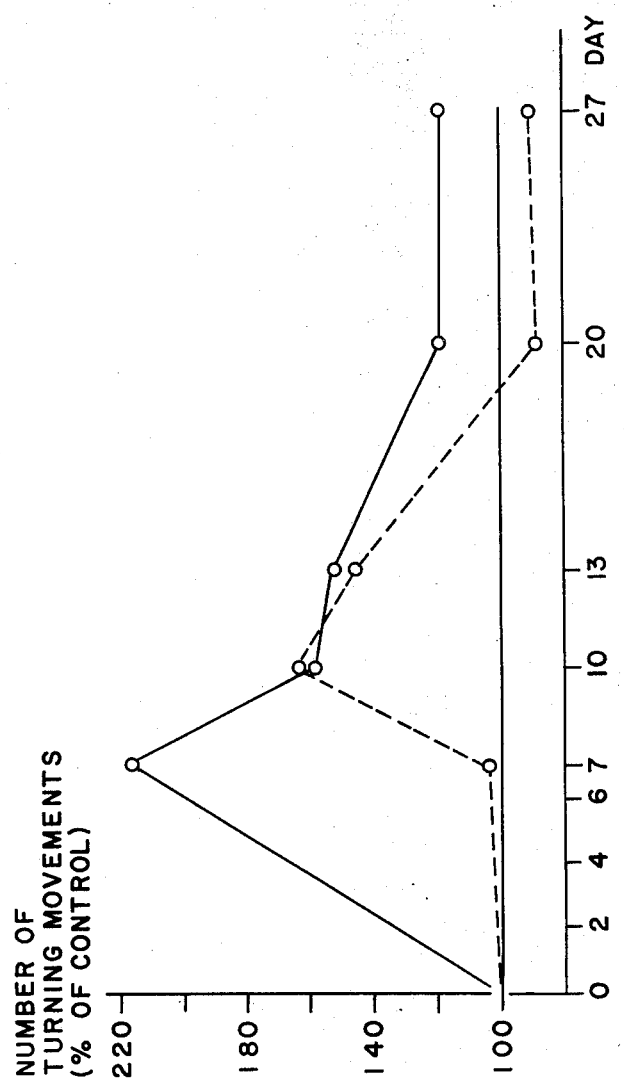

FIG. 4: Turning movements after apomorphine in rats with unilateral lesions in the striatum. Pretreatment by repeated administration of haloperidol, with and without further addition of clozapine.

|     | 1st–6th day           | 7th day              |
|-----|-----------------------|----------------------|
| 0—0 | haloperidol 3 mg/kg p.o. | water 10 cc/kg p.o. |
| 0—0 | haloperidol 3 mg/kg p.o. | clozapine 20 mg/kg p.o. |
| 0—0 | water 10 mg/kg p.o.   | water 10 cc/kg p.o.  |

Apomorphine was administered (0.4 mg/kg s.c.) 3 hours after treatment on the seventh day and on the 10th, 13th, 20th and 27th day.

Rats having a weight of approx. 150 g are narcotized. Procaine with the addition of adrenalin is injected s.c. in the site of operation in order to suppress bleeding and postoperative indisposition to a great extent. The skull cap is then exposed and openings having a diameter of 0.8 mm are perforated in the right side of the skull 2 mm rostrally and 2.5 mm laterally and 0.5 mm rostrally and 3 mm laterally from the bregma. Electrodes having a diameter of 0.4 mm are introduced to a depth of about 5 mm in both perforations. A banana plug having the function of an inert electrode is introduced in the rectum. A lesion is performed in the corpus striatum by an electric shock whereby the intensity and duration of the electric shock required to cause a lesion in the striatum is ascertained in previous tests.

10 to 14 days after the operation, 0.4 mg/kg s.c. of apomorphine are administered to the animals, and the number of turning movements thus induced is ascertained during several successive 5-minute periods until turning movements stop (about 45 minutes). This procedure is repeated with 10 to 14 day intervals until the number of turning movements is quite constant. (Animals having too small or too large numbers of turning movements are removed). The remaining animals are divided into groups of 6 to 10 animals, taking into consideration that the average number of turning movements should be equal in all the groups. The rats are placed in individual cages about 30 minutes before the injection of apomorphine.

The test rats begin to perform a turning movement within 5 minutes after administration of apomorphine. During the following 5 minutes the number of turning movements increases and remains constant until about 20 minutes before decrease. The turning movements stop about 40 to 45 minutes after apomorphine administration. The effect of a unit dose of clozapine (10 or 20 mg/kg) or haloperidol (3 mg/kg) on the turning movement induced by apomorphine may be seen in FIGS. 1 and 2. Clozapine causes only a small reduction of the duration of turning movements and has no influence on turning speed. This leads to a small, but statistically significant decrease in the total number of turning movements as compared with the controls. Haloperidol completely stops every effect of apomorphine when administered 3 hours before apomorphine, and causes a slight, statistically insignificant increase in the total number of turning movements when administered 27 hours before apomorphine.

After oral administration on 6 successive days at doses of 20 or 80 mg/kg daily, clozapine has no influence on the turning movement which is induced 27 hours later by administration of apomorphine. Even treatment with higher doses of clozapine for a period of 13 or 20 days only causes a slight, statistically insignificant increase in the total number of turning movements. This differs from the effect of 6 daily doses of haloperidol (3 mg/kg p.o.) by which the number of turning movements induced by apomorphine is more than doubled as compared with the controls (FIG. 1). Haloperidol also increases the frequency and duration of turning movement as may be seen in FIG. 3. A potentiation of the apomorphine effect can still be ascertained one to two weeks after treatment with haloperidol is stopped (FIG. 4). The turning movements are antagonized on the seventh day by a further dose of haloperidol which is administered 3 hours before apomorphine administration, whereby the rats' reaction to apomorphine is a hasty sniffling.

Upon administration of clozapine (5, 10 or 20 mg/kg p.o.) in place of haloperidol on the seventh day, the hypersensibilization towards apomorphine induced by haloperidol is suppressed and the reaction of the animals is similar to the controls (FIG. 1).

The above tests indicate that after stopping chronic administration of haloperidol, the turning movements increase by more than 200 % (calculated on the controls) after administration of apomorphine, and even 27 hours after administration of a unit dose the reaction is increased slightly but not significantly. Clozapine, however, does not cause a change in the effect of apomorphine.

For the above mentioned use the dosage will, of course, vary depending on the compound employed, mode of administration and therapy desired. However, in general, satisfactory results are obtained when administered at a daily dosage of from 0.4 mg to about 80 mg per kg animal body weight, conveniently given in divided doses 2 to 4 times a day or in sustained release form. For the larger mammal, the total daily dosage is in the range from about 25 to about 200mg, and dosage forms suitable for oral administration comprise from about 6 mg to about 100 mg of the compounds admixed with a solid or liquid pharmaceutical carrier or diluent. Such compositions are known.

Clozapine may also be administered in the form of pharmaceutically tolerable acid addition salts thereof. These salts exhibit the same order of activity as the free bases and may be produced by reacting the free base with a suitable acid. Accordingly, the present invention also includes the therapeutic use of the salts of clozapine. The preferred salts are those with inorganic acids, such as hydrochloric acid, sulphuric acid, phosphoric acid, or with organic acids such as acetic acid, maleic acid, tartaric acid, citric acid, p-aminosalicylic acid, salicyclic acid and tannin.

Suitable compositions for oral administration are tablets which may be produced in accordance with known methods and containing the following ingredients: 2 mg of clozapine in hydrochloride form, 2 mg of magnesium stearate, 8 mg of polyvinyl pyrrolidone, 10 mg of talc, 20 mg of maize starch, 150 mg of lactose, 1 mg of dimethylsilicone oil and 3 mg of polyethylene glycol 6000.

I claim:

1. A method of treating dyskinesias in animals induced by the action of a dopaminergic substance useful in the treatment of Parkinson's desease on hypersensitive dopamine receptors, without blocking the receptors, which comprises administering 0.4 to 80 milligrams per kilogram of animal body weight of clozapine to an animal in need of such treatment.

2. A method according to claim 1, wherein the dopaminergic substance is DOPA.

3. A method of treating animals suffering from Parkinson's disease comprising administering to an animal in need of such treatment a therapeutically effective amount of a dopaminergic substance useful in treating Parkinson's desease and concomitantly 0.4 to 80 milligrams per kilogram of animal body weight per day of clozapine to suppress dyskinesias induced by administration of the dopaminergic substance.

4. A method according to claim 3, wherein the daily dosage of clozapine is from 25 to 200 milligrams.

5. A method according to claim 3, wherein clozapine is orally administered at a unit dose of 6 to 100 milligrams.

* * * * *